(12) United States Patent  
Ma et al.

(10) Patent No.: US 12,245,622 B2
(45) Date of Patent: Mar. 11, 2025

(54) XENON LAMP POWER SUPPLY, PURIFICATION DEVICE AND REFRIGERATION DEVICE

(71) Applicants: HEFEI MIDEA REFRIGERATOR CO., LTD., Hefei (CN); HEFEI HUALING CO., LTD., Hefei (CN); MIDEA GROUP CO., LTD., Foshan (CN)

(72) Inventors: Zhuobiao Ma, Hefei (CN); Zhen Zhang, Hefei (CN)

(73) Assignees: HEFEI MIDEA REFRIGERATOR CO., LTD., Hefei (CN); HEFEI HUALING CO., LTD., Hefei (CN); MIDEA GROUP CO., LTD., Foshan (CN)

( * ) Notice: Subject to any disclaimer, the term of this patent is extended or adjusted under 35 U.S.C. 154(b) by 270 days.

(21) Appl. No.: 17/925,316

(22) PCT Filed: Dec. 27, 2021

(86) PCT No.: PCT/CN2021/141550
§ 371 (c)(1),
(2) Date: Nov. 15, 2022

(87) PCT Pub. No.: WO2022/161066
PCT Pub. Date: Aug. 4, 2022

(65) Prior Publication Data
US 2023/0189849 A1  Jun. 22, 2023

(30) Foreign Application Priority Data
Jan. 26, 2021 (CN) .......................... 202110105972.7

(51) Int. Cl.
*A23L 3/28* (2006.01)
*A23L 3/00* (2006.01)
(Continued)

(52) U.S. Cl.
CPC .................. *A23L 3/28* (2013.01); *A23L 3/001* (2013.01); *A23L 3/003* (2013.01); *A61L 2/08* (2013.01);
(Continued)

(58) Field of Classification Search
CPC . A23L 3/28; A23L 3/001; A23L 3/003; A61L 2/08; A61L 2/26; A61L 2202/11;
(Continued)

(56) References Cited

U.S. PATENT DOCUMENTS

2003/0019222 A1   1/2003  Takahashi et al.
2009/0289557 A1  11/2009  Itoh et al.
(Continued)

FOREIGN PATENT DOCUMENTS

CN    1076912 A  * 10/1993  ............. C01B 13/10
CN    2930191 Y     8/2007
(Continued)

OTHER PUBLICATIONS

EESR received in EP Application No. 21922655.2; mailed Sep. 11, 2023.
(Continued)

*Primary Examiner* — Abdullah A Riyami
*Assistant Examiner* — Syed M Kaiser

(57) ABSTRACT

An xenon lamp power supply, a purification device, and a refrigeration device are provided. The xenon lamp power supply comprises: an input circuit, a coupling assembly, an output circuit, and a control circuit. The input circuit comprises an alternating-current input end and a direct-current output end, and the input circuit is used for converting alternating current input by the alternating-current input end into direct current output by the direct-current output end. A first end of the coupling assembly is connected to the direct-current output end. The output circuit comprises a
(Continued)

xenon lamp power supply circuit, and the xenon lamp power supply circuit is connected to a second end of the coupling assembly, so as to convert electric energy from the second end into direct-current power, and then supply power to a xenon lamp.

12 Claims, 6 Drawing Sheets

(51) Int. Cl.
*A61L 2/08* (2006.01)
*A61L 2/26* (2006.01)
*F25D 17/04* (2006.01)
*H02M 3/335* (2006.01)

(52) U.S. Cl.
CPC .............. *A61L 2/26* (2013.01); *F25D 17/042* (2013.01); *H02M 3/335* (2013.01); *A61L 2202/11* (2013.01); *A61L 2202/121* (2013.01); *A61L 2202/122* (2013.01); *A61L 2202/14* (2013.01); *F25D 2317/0417* (2013.01)

(58) Field of Classification Search
CPC ......... A61L 2202/121; A61L 2202/122; A61L 2202/14; F25D 17/042; F25D 2317/0417; H02M 3/335; H02M 1/32; H02M 3/33507; H02M 3/003; H02M 1/0006; H02M 1/007; H02M 1/0064; H02M 1/36; H02M 7/06; H02M 1/348; H02M 3/33561; H02M 1/327; H02M 1/44; H05B 41/292; H05B 41/14; Y02B 20/00
See application file for complete search history.

(56) References Cited

U.S. PATENT DOCUMENTS

2016/0220095 A1\* 8/2016 Shimomura ........ A61B 1/00006
2017/0351297 A1\* 12/2017 Kim .................... H04M 1/0202

FOREIGN PATENT DOCUMENTS

| | | | | |
|---|---|---|---|---|
| CN | 201063052 | | 5/2008 | |
| CN | 101354426 | A | 1/2009 | |
| CN | 201533242 | U | 7/2010 | |
| CN | 102076741 | A \* | 5/2011 | ............ A23K 10/00 |
| CN | 203416169 | U | 1/2014 | |
| CN | 204290726 | U | 4/2015 | |
| CN | 106100388 | A | 11/2016 | |
| CN | 107070227 | A | 8/2017 | |
| CN | 107105536 | A \* | 8/2017 | ............ F21V 15/01 |
| CN | 108576552 | A | 9/2018 | |
| CN | 108809064 | A | 11/2018 | |
| CN | 209978478 | | 1/2020 | |
| CN | 111885763 | A | 11/2020 | |
| JP | 2002272105 | A | 9/2002 | |
| JP | 2011116767 | A \* | 6/2011 | ............ A01N 25/02 |
| JP | 2018063898 | A | 4/2018 | |
| JP | 2020048372 | A | 3/2020 | |
| KR | 20180005910 | A \* | 1/2018 | |
| KR | 20200061281 | A \* | 6/2020 | |
| WO | 2007069481 | A1 | 6/2007 | |
| WO | 2016194877 | A1 | 12/2016 | |

OTHER PUBLICATIONS

ISR mailed Mar. 10, 2022 of PCT Application No. PCT/CN2021/141550.
Japanese Patent Office, Decision of Rejection Issued in Application No. 2022-570198, Nov. 21, 2023, 4 pages.
First Search Report received in CN Application No. 202110105972.7; mailed Oct. 30, 2023.

\* cited by examiner

XENON LAMP POWER SUPPLY, PURIFICATION DEVICE AND REFRIGERATION DEVICE

CROSS-REFERENCES TO RELATED APPLICATIONS

The present disclosure is a national phase application of International Application No. PCT/CN2021/141550, filed on Dec. 27, 2021, which claims the priority to Chinese patent application No. 202110105972.7, filed on Jan. 26, 2021, the entireties of which are herein incorporated by reference.

FIELD

The application relates to the technical field of energy technology, and in particular, to a xenon lamp power supply, a purification device and a refrigeration equipment.

BACKGROUND

A traditional xenon lamp power supply usually adopts a digital power supply. A power output and PWM output of the entire power supply are controlled by a software, and a mode for controlling the software is easily to be limited by a processing speed of a MCU and related logic conditions, resulting in delayed response and poor control accuracy. In addition, this digital power supply is usually a non-electrically isolated power supply. Although a primary and a secondary of a transformer are used as an input and an output of the power supply respectively, its input and output have the same reference low potential due to a common ground connection, which leads to strong and weak electrical interference between the primary and secondary of the transformer, and has relatively low safety.

SUMMARY

The application provides a xenon lamp power supply, a purification device and a refrigeration device to solve the problems in the related art that a xenon lamp digital power supply does not response in time and has poor control accuracy, and the xenon lamp digital power supply is non-electrically isolated, resulting in the existence of strong and weak electric and electromagnetic interference, to achieve stable and reliable power supply for the xenon lamp.

The application provides a xenon lamp power supply, including:
- an input circuit, including an AC input end and a DC output end and configured to convert an AC input from the AC input end to a DC output from the DC output end;
- a coupling assembly, where a first end of the coupling assembly is connected to the DC output end;
- an output circuit, including a xenon lamp power supply circuit connected to a second end of the coupling assembly to convert an electric energy from the second end of the coupling assembly to a strong DC for powering a xenon lamp;
- a control circuit, connected to the first end and a third end of the coupling assembly respectively and configured to control an electric energy of the first end of the coupling assembly to transmit the electric energy to the second end and the third end of the coupling assembly by electromagnetic coupling, where the third end of the coupling assembly supplies power to the control circuit.

According to the xenon lamp power supply provided by the present application, the output circuit further includes an auxiliary power supply circuit, where the auxiliary power supply circuit is connected to a fourth end of the coupling assembly and is configured to convert an electric energy from the fourth end to a weak DC and output the weak DC.

According to the xenon lamp power supply provided by the present application, the xenon lamp power supply further includes a feedback circuit, where the feedback circuit is connected to the xenon lamp power supply circuit and the auxiliary power supply circuit respectively to detect a voltage of the strong DC output by the xenon lamp power supply circuit, and cooperates with the weak DC provided by the auxiliary power supply circuit to generate a detection signal of the voltage of the strong DC output by the xenon lamp power supply circuit, and feeds the detection signal back to the control circuit.

According to the xenon lamp power supply provided by the present application, the control circuit is configured to adjust an on-off duty cycle of the first end of the coupling assembly according to the detection signal, to change the voltage of the strong DC output by the xenon lamp power supply circuit.

According to the xenon lamp power supply provided by the present application, the xenon lamp power supply further includes a shielding circuit, where one end of the shielding circuit is connected to the control circuit and another end of the shielding circuit is grounded, and the shielding circuit is configured to shield an open-circuit state of the feedback circuit.

According to the xenon lamp power supply provided by the present application, the xenon lamp power supply further includes an overvoltage protection circuit, where the overvoltage protection circuit is connected to the control circuit and a fifth end of the coupling assembly respectively, and the overvoltage protection circuit is configured to perform overvoltage protection on the control circuit when the strong DC output by the xenon lamp power supply circuit is greater than a preset value, where the fifth end of the coupling assembly is in the same phase as the first end of the coupling assembly.

According to the xenon lamp power supply provided by the present application, the xenon lamp power supply further includes a startup circuit, where the startup circuit is connected to the control circuit and the input circuit respectively, to start the control circuit through the electric energy provided by the input circuit.

According to the xenon lamp power supply provided by the present application, the xenon lamp power supply further includes an absorption circuit, where the absorption circuit is provided between the control circuit and the first end of the coupling assembly, to absorb a surge voltage when the control circuit controls the first end of the coupling assembly to transmit an electric energy by electromagnetic coupling.

According to the xenon lamp power supply provided by the present application, the xenon lamp power supply further includes a power supply state detection circuit, where the power supply state detection circuit is connected to the auxiliary power supply circuit to detect whether the output state of the auxiliary power supply circuit is abnormal, and feeds it back to the control circuit when the output state of the auxiliary power supply circuit is abnormal, and the control circuit can perform abnormal processing.

According to the xenon lamp power supply provided by the present application, the xenon lamp power supply further includes a power-off control circuit, where the power-off control circuit is connected to the power supply state detection circuit, to feed it back to the control circuit when the output state of the auxiliary power supply circuit is abnormal, and the control circuit can turn off the xenon lamp power supply.

The present application further provides a purification device for refrigeration equipment, the refrigeration equipment includes a compartment, a refrigeration system for refrigerating the compartment, and a door body for opening and closing the compartment, where the purification device includes:

the above-mentioned xenon lamp power supply, configured to supply power to the xenon lamp assembly, where the xenon lamp assembly is a xenon lamp provided in the compartment to purify food stored in the compartment during flashing.

The present application further provides a refrigeration equipment, comprising: the purification device according to the above refrigeration equipment.

According to the refrigeration equipment provided by the present application, the refrigeration equipment is a refrigerator, and the compartment is a refrigerating chamber and/or a temperature variable chamber of the refrigerator.

The present application provides a xenon lamp power supply, a purification device and a refrigeration equipment. The xenon lamp power supply includes an input circuit, a coupling assembly, an output circuit and a control circuit. The input circuit includes an AC input end and a DC output end and is configured to convert an AC input from the AC input end to a DC output from the DC output end; the first end of the coupling assembly is connected to the DC output end to convert the voltage of the DC output end to the other ends of the coupling assembly; the second end of the coupling assembly is connected to the xenon lamp power supply circuit of the output circuit to convert the electric energy from the second end to strong DC to supply power to the xenon lamp; the control circuit is connected to the first end and the third end of the coupling assembly respectively and is configured to control the electric energy of the first end of the coupling assembly to transmit the electric energy to the second end and the third end of the coupling assembly by electromagnetic coupling, where the third end supplies power to the control circuit. The overall circuit hardware structure is optimized, which completely gets rid of the situation that the xenon lamp power supply is limited by software logic control in the related art. With cooperation between each of the circuit modules and the coupling assembly being designed to have several ends for input and output, a primary winding and a secondary winding are in completely independent electrical isolation state, which can avoid the electromagnetic interference between the primary and secondary windings, and improve the safety protection level and power supply performance of the xenon lamp power supply, and has the advantages of high safety and stable output. The overall design of the circuit structure of the xenon lamp power supply, by using an electrically isolated low-power analog power supply, a power output index can only be met by a high-power power supply in the related art is achieved, and power can be supplied to the xenon lamp stably and reliably, to ensure rapid and continuous flashing of the xenon lamp.

BRIEF DESCRIPTION OF THE DRAWINGS

In order to illustrate the solutions in the present application or the related art more clearly, the accompanying drawings required in the description of the embodiments or the related art will be briefly introduced below. The accompanying drawings in the following description are some embodiments of the application. For those of ordinary skill in the art, other drawings can also be obtained according to these drawings without any creative effort.

DETAILED DESCRIPTION OF THE DISCLOSURE

In order to make the purpose, solutions and advantages of the present application clearer, the technical solutions in the present application will be described clearly and completely below with reference to the accompanying drawings in the present application. The described embodiments are part of the embodiments of the present application, rather than all. Based on the embodiments in the present application, all other embodiments obtained by those of ordinary skill in the art without creative effort fall within the protection scope of the present application.

A xenon lamp power supply, a purification device and a refrigeration equipment provided by the present application are described below with reference to FIG. 1 to FIG. 11.

Figure 1:
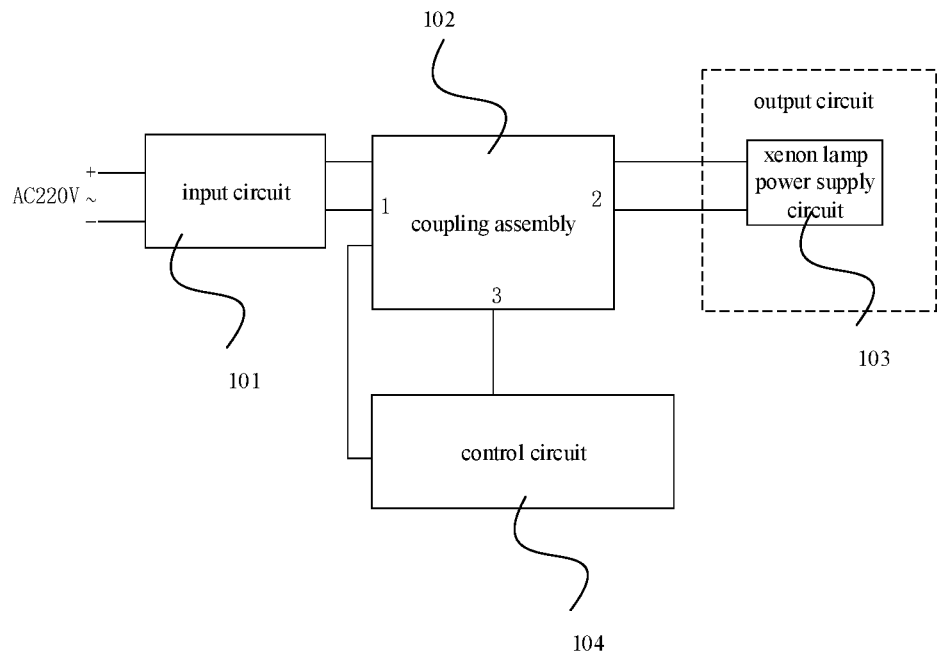
FIG. 1 is one of the structural schematic diagrams of a xenon lamp power supply provided by the application.

The application provides a xenon lamp power supply. FIG. 1 is one of the schematic diagrams of a structure of the xenon lamp power supply provided by the application. As shown in FIG. 1, the xenon lamp power supply includes: an input circuit 101, a coupling assembly 102, an output circuit and a control circuit 104, where the input circuit 101 includes an AC input end and a DC output end, and the input circuit 101 is configured to convert the AC input from the AC input end to the DC output from the DC output end. When the xenon lamp power supply is powered on, the AC input end is connected to the mains electricity to obtain 220 V AC from the mains electricity.

A first end of the coupling assembly 102 (at the reference number 1 in FIG. 1) is connected to the DC output end of the input circuit 101.

The output circuit includes a xenon lamp power supply circuit 103 which is connected to a second end (at the reference number 2 in FIG. 1) of the coupling assembly 102, to convert an electric energy from the second end of the coupling assembly 102 to a strong DC for powering a xenon lamp.

The control circuit 104 is connected to the first end and a third end (at the reference numbers 1 and 3 in FIG. 1) of the coupling assembly 102 respectively and is configured to control an electric energy of the first end of the coupling assembly 102 to transmit the electric energy to the second end and the third end of the coupling assembly 102 by electromagnetic coupling, where the third end of the coupling assembly supplies power to the control circuit 104.

The xenon lamp power supply provided in the present application includes an input circuit 101, a coupling assembly 102, an output circuit and a control circuit 104. The input circuit 101 includes an AC input end and a DC output end and is configured to convert an AC input from the AC input end to a DC output from the DC output end; the first end of the coupling assembly 102 is connected to the DC output end to convert the voltage of the DC output end to the other ends of the coupling assembly 102; the second end of the coupling assembly 102 is connected to the xenon lamp power supply circuit 103 of the output circuit to convert the electric energy from the second end to strong DC to supply power to the xenon lamp; the control circuit 104 is connected to the first end and the third end of the coupling assembly 102 respectively and is configured to control the electric energy of the first end of the coupling assembly 102 to transmit the electric energy to the second end and the third end of the coupling assembly 102 by electromagnetic coupling, where the third end supplies power to the control circuit 104.

The overall circuit hardware structure is optimized, which completely gets rid of the situation that the xenon lamp power supply is limited by software logic control in the related art. With cooperation between each of the circuit modules and the coupling assembly being designed to have several ends for input and output, a primary winding and a secondary winding are in completely independent electrical isolation state, which can avoid the electromagnetic interference between the primary and secondary windings, and improve the safety protection level and power supply performance of the xenon lamp power supply, and has the advantages of high safety and stable output. The overall design of the circuit structure of the xenon lamp power supply, by using an electrically isolated low-power analog power supply, a power output index can only be met by a high-power power supply in the related art is achieved, and power can be supplied to the xenon lamp stably and reliably, to ensure rapid and continuous flashing of the xenon lamp. The electrically isolated low-power analog power supply is used, that is, a power margin required by the xenon lamp power supply becomes smaller. For example, the power margin of the xenon lamp power supply is reduced from 5 times or 10 times to 1.6 times. The size and volume of the xenon lamp power supply itself is largely reduced, thereby the production cost of the xenon lamp power supply is greatly saved.

Figure 2:
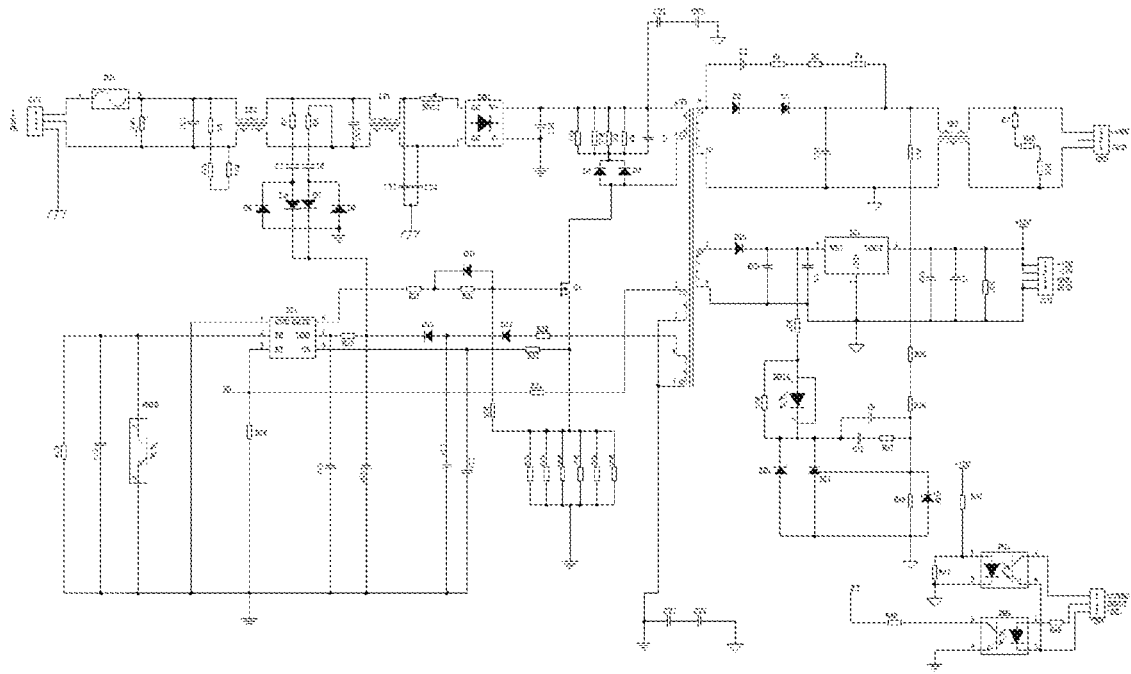
FIG. 2 is a schematic diagram of a circuit principle of a xenon lamp power supply provided by the application.

FIG. 2 is a schematic diagram of a circuit principle of a xenon lamp power supply provided by the application. As shown in FIG. 1 and FIG. 2, in an embodiment, the input circuit 101 includes an AC input end and a DC output end. When the xenon lamp power supply needs to be powered on, the AC input end is connected to the mains electricity through a connector CN1 to obtain 220V AC from the mains electricity.

Between the AC input end and the DC output end, the input circuit 101 further includes a fuse module, a pressure sensitive module, an electromagnetic filter module and a primary rectifier module which are connected in sequence. The fuse module adopts a fuse HA which is configured to fuse to protect the entire power supply when an over high voltage is input. The pressure-sensitive module adopts a varistor VR1. The electromagnetic filter module or EMC filter module is connected in parallel to the varistor VR1 and then connected in series between the neutral and live wires of the circuit. Specifically, the EMC filter module includes a capacitor CX1 and a capacitor CX2 are connected in parallel with each other, and a common mode inductor LF1 and a common mode inductor LF2 connected in series with each other to form a filter network collectively, to suppress or even eliminate strong electromagnetic interference or electrical spark interference in the current. The EMC filter module may further include a capacitor voltage discharge circuit formed by three resistors, a resistor R15, a resistor R16 and a resistor R17 in series, as shown in FIG. 2. The capacitor voltage discharge circuit is connected in parallel to two ends of a capacitor CX1 or CX2 and is configured to quickly reduce the residual voltage in the plug to a safe voltage range to human body when the xenon lamp power supply is disconnected from the mains electricity or the power plug is unplugged, for example, residual voltage is reduced to below 36 V within 1 s. In addition, the EMC filter module may further include an EMC debugging circuit, the EMC debugging circuit is composed of capacitors CY3 and CY4 whose one ends are collectively connected to the ground and another ends are respectively connected to two ends of the EMC filter module, which can effectively debug the filtering effect of the EMC filter module.

The primary rectifier module includes a rectifier bridge DB1 and a capacitor EC1 whose two ends are respectively connected to the V+ end and the V− end of the rectifier bridge DB1, and one end of the capacitor EC1 connected to the V− end is grounded. The primary rectifier module further includes a surge suppressor NTC1 provided at an AC input end of the rectifier bridge DB1 and is configured to suppress a surge current generated by the capacitor EC1 at the moment when the xenon lamp power supply is powered on. The output of the EMC filter module is still AC, which is input through the two AC ends of the rectifier bridge DB1. After the AC is rectified and filtered, a DC voltage is output through the V+ end of the rectifier bridge DB1. The V+ end of the rectifier bridge DB1 is used as a DC output end to output a DC voltage of 310 V converted from a AC 220 V voltage as a DC.

The first end of the coupling assembly 102 (the coupling assembly is a transformer T1, the first end corresponds to the reference number 1 in FIG. 1 and the primary winding 4-6 of the transformer T1 in FIG. 2) is connected to the DC output end of the input circuit 101 and is configured to receive a DC of 310 V. And because the control circuit 104 controls the first end of the coupling assembly 102, the DC voltage of 310 V can be turned into an AC voltage with a certain fluctuation rule (which can be understood as a pulse voltage), and then the AC voltage is used as the basis for the transformer T1 to perform transformation processing.

The transformer T1 transforms a AC voltage according to the transformation ratio of the corresponding winding, and a second end of the transformer T1 obtains a transformed AC voltage with a certain regularity (which can also be understood as a pulse voltage). The output circuit includes a xenon lamp power supply circuit 103, and the xenon lamp power supply circuit 103 is connected to the second end of the transformer T1 (the reference number 2 in FIG. 1, corresponding to the secondary windings 9-10 of the transformer T1 in FIG. 2), so that the xenon lamp is powered based on a strong DC of 300V, after the pulse voltage from the second end is converted to the strong DC of 300V.

With reference to FIG. 2, as a main output circuit of the secondary of the transformer T1, the xenon lamp power supply circuit 103 specifically includes a main output rectification and filtering module, an EMC improvement module and a virtual load module which are connected in sequence. The main output rectification and filtering module is composed of a diode D1, a diode D2 and a filter capacitor EC2, and is configured to rectify and filter the pulse voltage output by the secondary windings 9-10 of the transformer T1, and convert it to strong DC of 300V. The EMC improvement module adopts a common mode inductor LF3, which can effectively reduce the electromagnetic interference in the circuit and improve the voltage quality. The virtual load module is composed of a resistor R7, a resistor R12 and a resistor R14 connected in series and then connected in parallel to two ends of the common mode inductor LF3, and can effectively act as an end load of the xenon lamp power supply circuit 103 to improve the no-load characteristics of the entire xenon lamp power supply. If a condition that an end-no-load of the xenon lamp power supply circuit 103 can meet the requirement of the stability of the power supply of the xenon lamp, the end-no-load can be reserved without the virtual load module. The xenon lamp power supply circuit 103 may further include a peak voltage absorption circuit connected in parallel to the main output rectification and filtering module, and the peak voltage absorption circuit is composed of a capacitor C2, a resistor R1, a resistor R2 and a resistor R3 connected in series in sequence and is configured to absorb a reverse peak voltage generated on the diode D1 and the diode D2 caused by leakage inductance or parasitic parameters, etc. and suppress a ringing phenomenon, when the main output rectification and filtering module processes a AC voltage.

The control circuit 104 is respectively connected to the first end (the first end corresponds to the reference number 1 in FIG. 1, and corresponds to the primary winding 4-6 of the transformer T1 in FIG. 2) and a third end (the third end is at the reference number 3 in FIG. 1 and corresponds to the primary winding 1-5 of the transformer T1 in FIG. 2) of the coupling assembly 102, and is configured to control the electrical energy of the first end of the coupling assembly 102 to transmit the electrical energy to the second end and the third end of the coupling assembly 102 by electromagnetic coupling. The primary winding 1 of the transformer T1 is still a forward winding. The control circuit 104 controls the first end of the coupling assembly 102 mainly by adjusting the switching frequency and on-off duty cycle of the power switch tube, which can effectively convert the DC voltage of 310 V to an AC voltage with a certain fluctuation rule, and then the AC voltage is used as the basis for the transformer T1 to perform voltage transformation. In addition, a DC voltage output by the third end of the transformer T1 after transformation is mainly configured to supply power to the control circuit 104.

In an embodiment, referring to FIG. 2, the control circuit 104 includes a power switch transistor Q1 for controlling the first end of the transformer T1 (primary winding 4-6) and a first power management chip IC1 for controlling the power switch transistor Q1. A D pole of the power switch transistor Q1 is connected to the first end of the coupling assembly 102. The first power management chip IC1 has 6 pins, which are a GND pin for grounding, a FB pin for receiving feedback signal, a RT pin for reference setting, a CS pin for current sensing protection, a VDD pin for inputting the operating voltage, and a GATE pin for outputting a PWM pulse drive signal. The voltage output by the third end of the transformer T1 (primary winding 1-5) is divided by a resistor R28, a diode D13, a diode D12, and a resistor R29 in sequence, and then filtered by the control circuit filtering module composed of a capacitor EC5, a capacitor EC6 and a capacitor C12. As a result, a voltage is generated as the operating voltage and is input into the VDD pin of the first power management chip IC1, so that the first power management chip IC1 can work.

The GATE pin is connected to a G pole of the power switch transistor Q1 to drive the power switch transistor Q1 to turn on or off by outputting a PWM pulse drive signal, or the power switch transistor Q1 is driven by the PWM pulse drive signal to work in on-off state with an operating frequency of several tens of KHz. A resistor R25 and a resistor R26 are further connected in series between the GATE pin and the power switch transistor Q1. The resistor R25 and the resistor R26 are connected to the G pole of the switch power transistor Q1 and further serve as a gate drive resistor of the switch power transistor Q1, and are connected to a S pole of the switching power transistor Q1 after connected in series to the gate bias resistor R35 of the switching power transistor Q1. The resistor R26 is further connected in parallel to a diode D11. The diode D11 can improve the speed to turn-off the power switch transistor Q1 to reduce its loss. The high-speed switch of the power switch transistor Q1 cooperates with the primary winding 4-6 of the transformer T1 to continuously transmit the electric energy of the primary of the transformer T1 to the secondary of the transformer T1, and the primary winding 4-6 stores electric energy when the power switch transistor Q1 is turned on, and transmits the electric energy to the secondary of the transformer T1 when the power switch transistor Q1 is turned off.

The S pole of the power switch transistor Q1 is further connected to a control circuit current sampling module composed of a resistor R39, a resistor R40, a resistor R41, a resistor R42, a resistor R43 and a resistor R44. One end of the control circuit current sampling module is connected to the S pole of the power switch transistor Q1, and further connected to the GATE pin of the first power management chip IC1 through a resistor R35, a resistor R25 and a resistor R26. Another other end of the control circuit current sampling module is grounded. Therefore, by setting or adjusting the resistor value of each resistor in the control circuit current sampling module, the PWM pulse drive signal output by the first power management chip IC1 can be effectively affected and the maximum output power of the output circuit is limited by the on-off of the switching power transistor Q1. The resistor R25 can further be configured to debug the EMC filter module.

The CS pin is connected to the S pole of the switch power transistor Q1 through a resistor R31, and is further grounded through a capacitor C13, to protect the first power management chip IC1. For example, when the end voltage of the CS pin reaches a certain threshold, the first power management chip IC1 is controlled to stop external output, to realize overcurrent protection. The FB pin is configured to receive a feedback signal from the output circuit, and control the PWM pulse drive signal output by the GATE pin according to the feedback signal of the output circuit, to control the primary winding 4 of the transformer T1 by controlling the power switch transistor Q1 (the first end of the coupling assembly 102). The feedback signal of the output circuit is input into the first power management chip IC1 through the FB pin, which can affect the on-off duty cycle of the power switch transistor Q1. Thereby, the power switch transistor Q1 control the DC voltage of 310 V on the primary winding 4-6 of the transformer T1 become an AC voltage with a certain fluctuation rule, so that the AC voltage is taking as an initial voltage for the transformer T1 to perform transformation processing.

The xenon lamp power supply provided by this application adopts a hardware circuit design, which completely gets rid of the situation that the xenon lamp power supply is limited by software logic control in the related art. For the conversion of power supply electric energy, only a single conversion of the xenon lamp power supply circuit from the input circuit 101 to the output circuit is performed, a strong DC voltage of 300 V can be output, which is completely different from the two-stage power conversion in existing technology that first a AC voltage of 22 V is converted into a DC voltage of 12 V through AC-DC rectification, and then the DC voltage of 12 V is converted into a DC voltage of 300 V through DC rectification. This application simplifies the conversion process of the power output, and improves the efficiency of power supply and reduces the cost of power supply. Moreover, the xenon lamp power supply can not only drag a single xenon lamp to perform flashing, but also can drag two or more xenon lamps to perform flashing synchronously or alternately. In addition, when a plurality of xenon lamps are simultaneously dragged for flashing, the electric energy output by the xenon lamp power supply can be utilized to a greater extent, which improves the electric energy utilization efficiency and reduces the power supply cost.

In the design process of the circuit structure of the xenon lamp power supply, since the output circuit is to output strong DC of 300 V, and the turns ratio and parasitic parameters of the transformer T1 will cause the main output winding 9-10 of the secondary of the transformer T1 to have peak voltage, and the peak voltage is about 1.3 KV, the transformer T1 prone to a problem of non-insulation or excessive temperature rise. Therefore, the transformer T1 adopts triple insulated wires and cooperates with the wide-span skeleton of a PQ2625 magnetic core, which can ensure the insulation safety and overcome the problem of excessive temperature rise.

Figure 3:
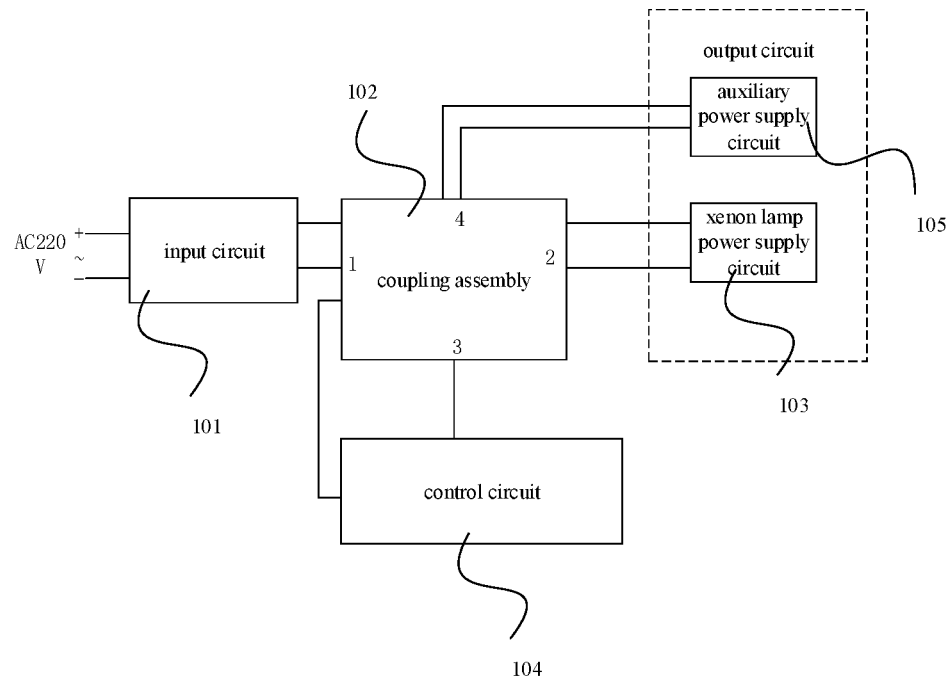
FIG. 3 is the second structural schematic diagram of a xenon lamp power supply provided by the application.

According to a xenon lamp power supply provided by the present application, FIG. 3 is a second structural schematic diagram of a xenon lamp power supply provided by the present application. As shown in FIG. 3, in the xenon lamp power supply, in addition to the xenon lamp power supply circuit 103, the output circuit further includes an auxiliary power supply circuit 105. The auxiliary power supply circuit 105 is connected to a fourth end of the coupling assembly 102 (the reference number 4 in the figure, corresponding to the secondary winding 7-8 of the transformer T1 in FIG. 2). The auxiliary power supply circuit 105 is configured to convert an electrical energy from the fourth end to a weak DC and output it.

As shown in FIG. 2, the auxiliary power supply circuit 105 includes an auxiliary output rectification and filtering module, a capacitor C8, a second power management chip IC2, a capacitor EC4, a capacitor C7 and a resistor R23 connected in sequence, where the auxiliary output rectification and filtering module is connected in parallel to two ends of the secondary winding 7-8 of the transformer T1, and the auxiliary output rectification and filtering module includes a diode D10 and a filter capacitor EC3 connected to each other and is configured to rectify the voltage on the secondary winding 7-8 of the transformer T1 and convert it to a DC voltage of 15 V. A VIN end of the second power management chip IC2 is configured to input, the VOUT end is configured to output, and the second power management chip IC2 further has a ground end GND. The second power management chip IC2 is configured to convert a DC voltage of 15 V into a DC voltage of 12 V. The capacitor EC4, the capacitor C7 and the resistor R23 are connected in parallel to the VOUT end and the ground end GND of the second power management chip IC2, and are connected in parallel to the connector CN3 to provide a DC voltage of 12 V to the outside.

Figure 4:
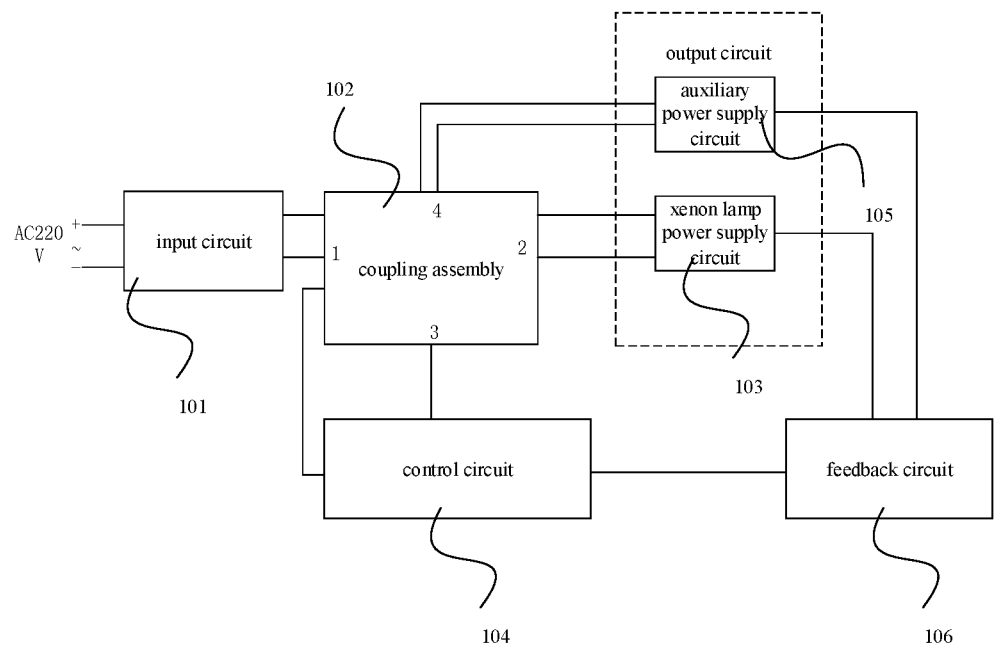
FIG. 4 is a third structural schematic diagram of a xenon lamp power supply provided by the application.

According to a xenon lamp power supply provided by the present application, FIG. 4 is a third structural schematic diagram of a xenon lamp power supply provided by the present application. As shown in FIG. 4, the xenon lamp power supply further includes: a feedback circuit 106 which is connected to the xenon lamp power supply circuit 103 and the auxiliary power supply circuit 105 respectively to detect a voltage of the strong DC output by the xenon lamp power supply circuit 103, and cooperates with the weak DC provided by the auxiliary power supply circuit 105 to generate a detection signal of the voltage of the strong DC output by the xenon lamp power supply circuit 103, and feeds the detection signal back to the control circuit 104.

With reference to FIG. 2, the feedback circuit 106 may include a main output circuit sampling circuit, an auxiliary output circuit sampling circuit, a frequency compensation circuit, a comparison voltage regulation circuit and an optocoupler feedback circuit. The main output circuit sampling circuit is composed of a sampling resistor R13, a sampling resistor R30, a sampling resistor R34 and a resistor R46 connected in series in sequence and is configured to obtain the sampling voltage of the main circuit from the high voltage side of the xenon lamp power supply circuit, and the main output circuit sampling circuit is connected to the frequency compensation circuit. The auxiliary output circuit sampling circuit adopts a resistor R27 to obtain the sampling voltage of the auxiliary power supply circuit from the high voltage side of the auxiliary power supply circuit.

The optocoupler feedback circuit and the comparison voltage regulation circuit are connected in series and are provided between the auxiliary output circuit sampling circuit and the main output circuit sampling circuit. The comparison voltage regulation circuit adopts a comparison voltage regulator IC3. The main output circuit sampling circuit transmits a sampled voltage obtained by dividing a DC strong voltage of 300 V output from the main output circuit of the xenon lamp power supply circuit to the reference end of the comparison voltage regulator IC3. The comparison regulator IC3 compares a sampling voltage input by the reference end with its own internal reference voltage. If the sampling voltage of the reference end is higher than the internal reference voltage, the comparison regulator IC3 is turned on. If the sampling voltage of the reference end is lower than the internal reference voltage, the comparison regulator IC3 is turned off. The frequency compensation circuit is composed of a capacitor C11 and a resistor R37 connected in series which are then connected to a capacitor C9 in parallel, and the capacitor C9, and is configured to perform frequency compensation on the comparison regulator IC3 to improve the frequency response performance of the comparison regulator IC3.

The optocoupler feedback circuit further includes an optocoupler receiving end PH2B provided in the control circuit 104, in addition to the optocoupler transmitting end PH1A provided between the auxiliary output circuit sampling circuit and the comparison regulator IC3. The optocoupler transmitting end PH1A and the optocoupler receiving end PH2B associate a voltage signal at the output end with the control circuit through the principle of photoelectric coupling to adjust an input of the input end of the input circuit, thereby the feedback circuit is set. With reference to a specific structure of the control circuit, the FB pin of the first power management chip IC1 is connected to the optocoupler receiving end PH2B. The main output circuit sampling circuit, the auxiliary output circuit sampling circuit, the frequency compensation circuit, and the comparison voltage regulation circuit cooperate with each other to detect a voltage of the strong DC output by the xenon lamp power supply circuit 103, and generate a detection signal of the voltage of the strong DC output from the xenon lamp power supply circuit 103 by cooperating with the weak DC provided by the auxiliary power supply circuit 105. The optocoupler transmitting end PH1A in the optocoupler feedback circuit couples the detection signal to the optocoupler receiving end PH2B, and transmits it to the first power management chip IC1 through the FB pin. The detection signal is used as the feedback signal of the output circuit so that the first power management chip IC1 controls the PWM pulse drive signal output by the GATE pin according to the feedback signal of the output circuit. By controlling the on-off duty cycle of the power switch transistor Q1, the primary winding 4-6 of the transformer T1 (the first end of the coupling assembly 102) is controlled, and the power switch transistor Q1 control a DC voltage of 310 V on the primary winding 4-6 of the transformer T1 to be an AC voltage with a certain fluctuation rule, so that the AC voltage can be used as an initial voltage for the transformer T1 to perform transformation processing. It can further be understood that the xenon lamp power supply adopts a dual output design. The main output circuit outputs a strong DC of 300V, and the auxiliary output circuit outputs a weak DC of 12 V. Both of them jointly participate in the feedback link to effectively set the feedback closed-circuit.

According to a xenon lamp power supply provided by the present application, still referring to FIG. 4, the control circuit 104 is configured to adjust the on-off duty cycle of the first end of the coupling assembly 102 according to the detection signal, to change the voltage of the strong DC output by the xenon lamp power supply circuit 103.

Referring to FIG. 2 again, the first power management chip IC1 in the control circuit 104 adjusts the duty cycle of the PWM pulse drive signal output by the GATE pin according to the detection signal received by the FB pin, thereby the on-off duty cycle of the power switch transistor Q1 is adjusted, or the operating frequency of on and off of the power switch transistor Q1 can be adjusted according to the load conditions, thereby the on-off duty cycle of the primary winding 4-6 of the transformer T1 during working is adjusted to change the voltage of the strong DC output by the xenon lamp power supply circuit 103. For example, when a DC voltage output by the xenon lamp power supply circuit in the output circuit is greater than 300 V, the comparison regulator IC3 in the feedback circuit 106 compares a sampled voltage input from the reference end with its own internal reference voltage. If the sampled voltage of the reference end is higher than the internal reference voltage, the comparison regulator IC3 is turned on, the input current of the detection signal of the optocoupler transmitting end PH1A in the optocoupler feedback circuit is increased, and the optocoupler transmitting end PH1A couples the detection signal to the optocoupler receiving end PH2B and then transmits it to the FB pin of the first power management chip IC1. The end voltage of the FB pin is reduced, so that the first power management chip IC1 reduces the duty cycle of the PWM pulse drive signal output by the GATE pin. Thereby, the AC voltage with a certain fluctuation rule output by the primary windings 4-6 of the transformer T1 is further reduced by reducing the on-off duty cycle of the power switch transistor Q1, and finally the output voltage of the xenon lamp power supply circuit is reduced. The circuit control principle when the DC voltage output by the xenon lamp power supply circuit in the output circuit is less than 300 V is the same as the control method above, which can be referenced with each other.

Figure 5:
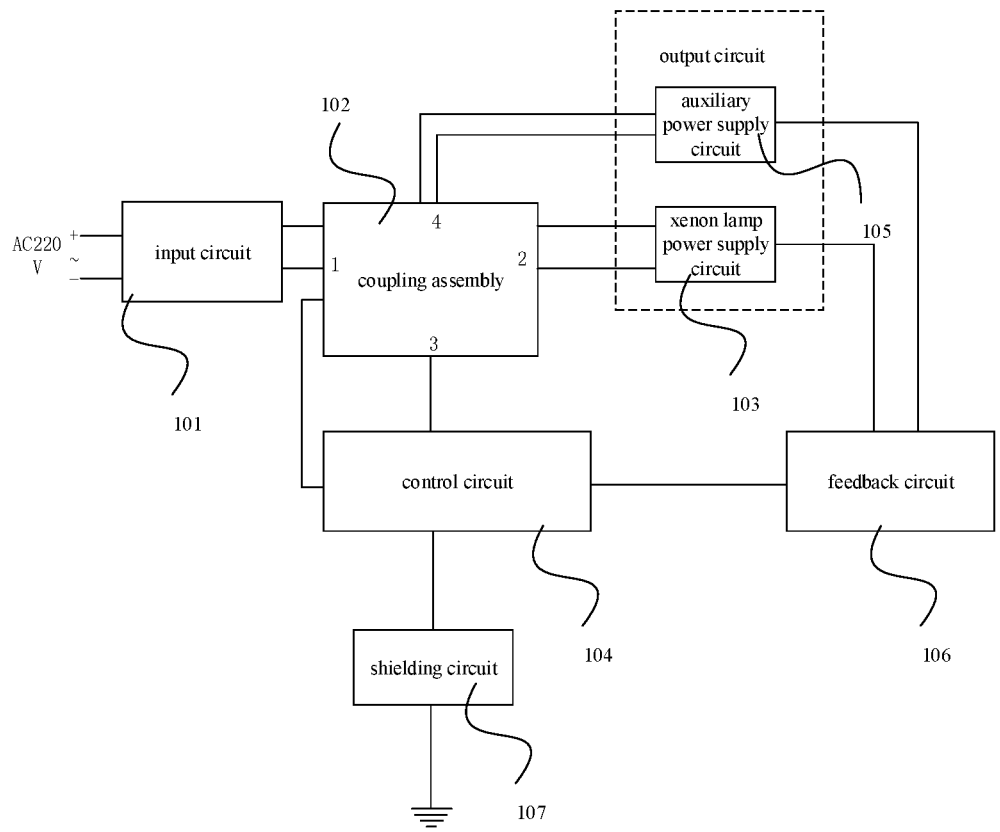
FIG. 5 is a fourth structural schematic diagram of a xenon lamp power supply provided by the application.

According to a xenon lamp power supply provided by the present application, FIG. 5 is a fourth structural schematic diagram of a xenon lamp power supply provided by the present application. As shown in FIG. 5, the xenon lamp power supply further includes: a shielding circuit 107 whose one end is connected to the control circuit 104 and another end is grounded, and the shielding circuit 107 is configured to shield an open-circuit state of the feedback circuit 106.

Referring to FIG. 2 again, the shielding circuit 107 is composed of a resistor R38, or the shielding circuit is composed of a resistor R38 and a capacitor C10 connected in parallel with each other. The shielding circuit is connected in parallel to the two ends of the optocoupler receiving end PH2B in the optocoupler feedback circuit, and one end of the shielding circuit 107 is connected to the control circuit 104, which means that one end of the shielding circuit is connected to the FB pin of the first power management chip, while another end of the shielding circuit is grounded. When the load of the output circuit is short-circuited, the overall feedback circuit will enter into an open-circuit state. After the feedback circuit is open-circuited for a certain period of time, the entire xenon lamp power supply will enter into an intermittent working mode, so that the xenon lamp power supply circuit 103 cannot quickly output a strong DC voltage of 300 V. The setting of the shielding circuit 107 can shield the open-circuit state of the feedback circuit 106, so that the xenon lamp power supply circuit 103 can quickly output a strong DC voltage of 300 V within 1 s for the xenon lamp to flash at the next time, after providing the xenon lamp with a strong DC voltage of 300 V. In other words, a power output index that can only be achieved by a traditional high-power power supply, such as a 200 W power supply, is reached by using an electrically isolated low-power analog power supply, such as a 48 W power supply, which effectively ensures the xenon lamp flashes quickly and continuously.

Figure 6:
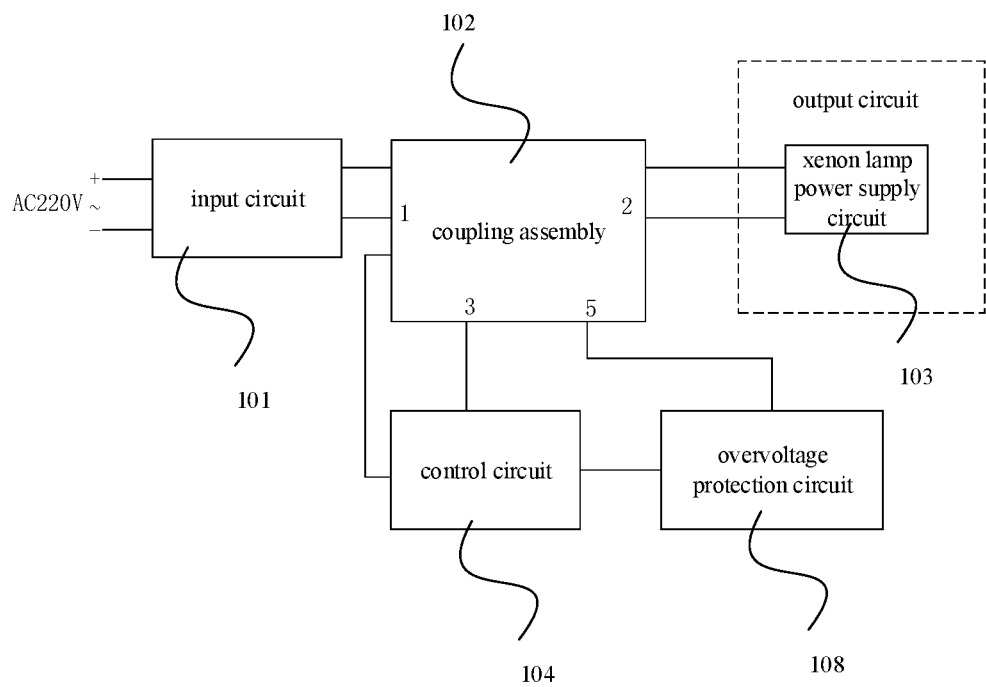
FIG. 6 is a fifth structural schematic diagram of a xenon lamp power supply provided by the application.

FIG. 6 is a fifth schematic diagram of the structure of a xenon lamp power supply provided by the present application. According to a xenon lamp power supply provided by the present application, as shown in FIG. 6, the xenon lamp power supply further includes an overvoltage protection circuit 108 which is connected to the control circuit 104 and a fifth end of the coupling assembly 102 respectively, and which is configured to perform overvoltage protection on the control circuit 104 when the strong DC output by the xenon lamp power supply circuit is greater than a preset value, where the fifth end of the coupling assembly 102 is in the same phase as the first end of the coupling assembly 102.

With reference to FIG. 2, the overvoltage protection circuit 108 is respectively connected to the control circuit 104 and the fifth end of the coupling assembly 102 (corresponding to the reference number 4 in FIG. 6, corresponding to the primary winding 2-3 of the transformer T1 in FIG. 2). It should be noted that the primary windings 1-2-3 of the transformer T1 are all forward windings. The overvoltage protection circuit 108 includes a resistor R32 and a resistor R36 respectively connected to the RT pin of the first power management chip IC1. Another end of the resistor R36 is grounded, and another end of the resistor R32 is connected to the primary winding 2 of the transformer T1. And the primary winding 3 of the transformer T1 and the primary winding 5 of the transformer T1 are grounded in common. The primary windings 2-3 of the transformer T1 is further kept in phase with the secondary windings 7-8 of the transformer T1 for detecting a output voltage of the output circuit. Therefore, a voltage divider network formed by the resistor R32 and the resistor R36 in the overvoltage protection circuit 108 can perform overvoltage protection on the control circuit 104, when an overvoltage occurs because of a strong DC output by the xenon lamp power supply circuit 103 being larger than a preset value.

Figure 7:
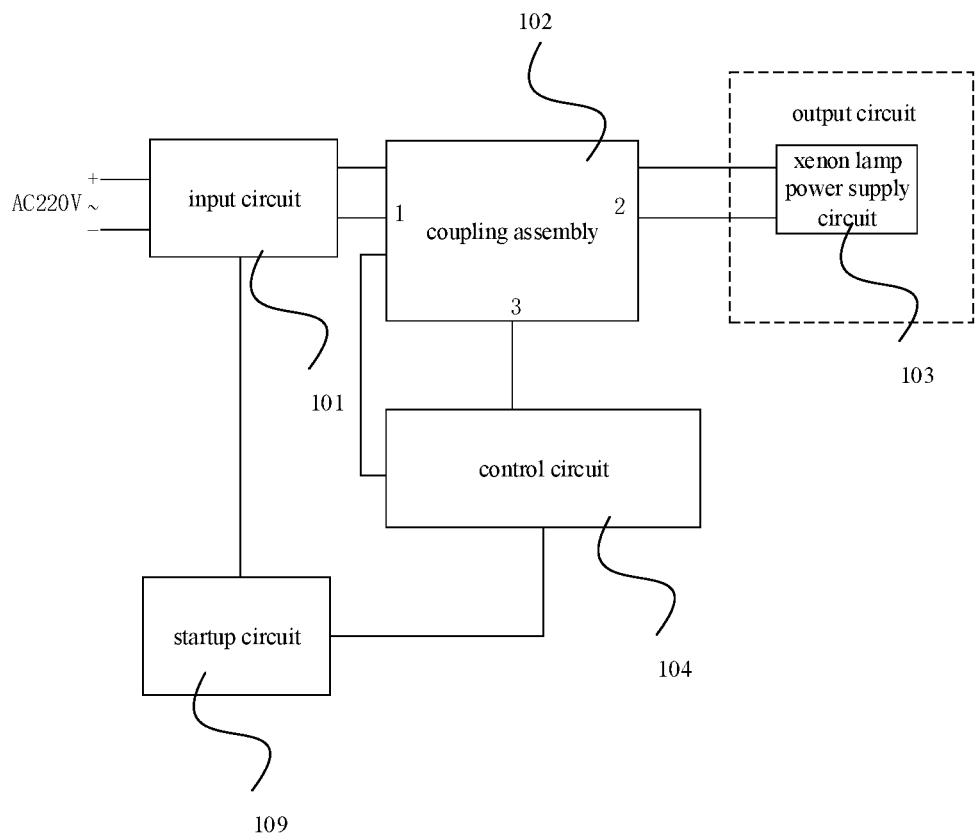
FIG. 7 is a sixth structural schematic diagram of a xenon lamp power supply provided by the application.

FIG. 7 is a sixth schematic diagram of the structure of a xenon lamp power supply provided by the present application. According to a xenon lamp power supply provided by the present application, as shown in FIG. 7, the xenon lamp power supply further includes: a startup circuit 109 which is connected to the control circuit 104 and the input circuit 101 respectively, to start the control circuit 104 with the electric energy provided by the input circuit 101.

Referring to FIG. 2 again, the startup circuit 109 is connected to the control circuit 104 and the input circuit 101 respectively. The startup circuit 109 includes a first startup branch composed of a resistor R9, a capacitor C5 and a diode D6 connected in series in sequence and a second startup branch composed of a resistor R4, a capacitor C6 and a diode D7 connected in series in sequence. One end of the first startup branch close to the resistor is connected to the high-voltage side of the common mode inductor LF2 of the input circuit 101, and one end of the second startup branch close to the resistor is connected to the low-voltage side of the common mode inductance LF2 of the EMC filter module, and another end of the first startup branch and another end of the second startup branch are connected to the VDD pin of the first power management chip IC1 via the resistor R29 to start the control circuit 104 with the power provided by the input circuit 101. An inverting diode D8 is further connected between the capacitor C5 and the diode D6 of the first startup branch, and an inverting diode D9 is further connected between the capacitor C6 and the diode D7 of the second startup branch, and the other ends of the inverting diode D8 and the inverting diode D9 are grounded in common. The startup circuit 109 provides a startup voltage for the operation of the first power management chip IC1, and the startup circuit 109 adopts the design that the resistance and the capacity cooperate with the diode, which can ensure that the static power consumption is not affected while the responsiveness of the xenon lamp power supply to instantaneous load short circuit is increased.

Figure 8:
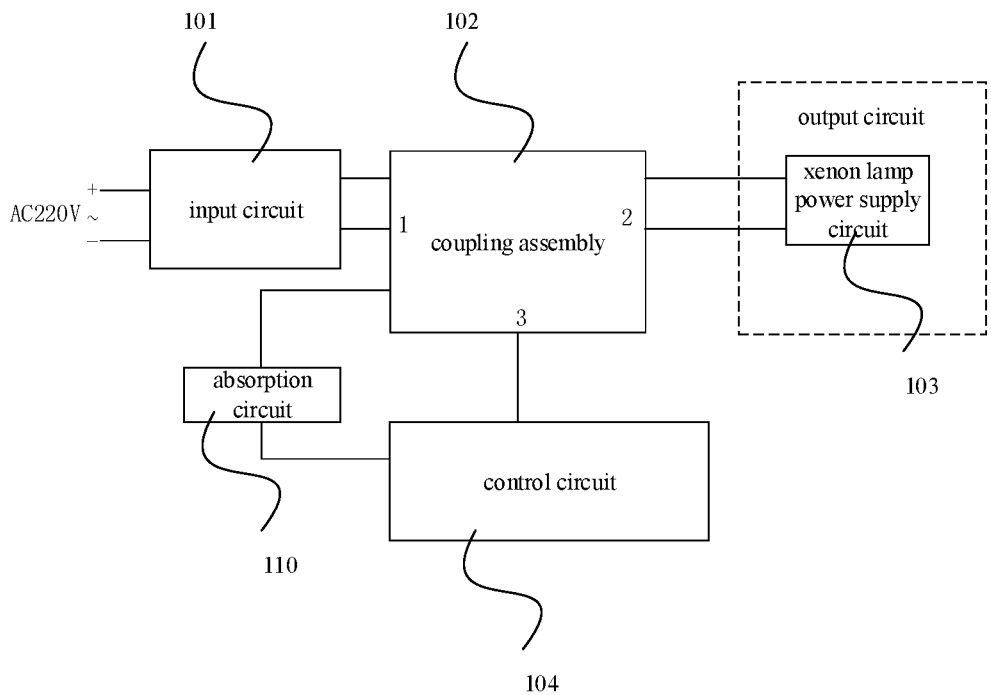
FIG. 8 is a seventh structural schematic diagram of a xenon lamp power supply provided by the application.

FIG. 8 is a seventh schematic diagram of the structure of a xenon lamp power supply provided by the present application. According to a xenon lamp power supply provided by the present application, as shown in FIG. 8, the xenon lamp power source further includes: an absorption circuit 110 which is provided between the control circuit 104 and the first end of the coupling assembly 102, to absorb a surge voltage when the control circuit 104 controls the first end of the coupling assembly 102 (corresponding to the reference number 1 in FIG. 8) transmit an electric energy by electromagnetic coupling.

Referring to FIG. 2 again, the absorption circuit 110, also called the RCD absorption circuit, is disposed between the control circuit 104 and the first end of the coupling assembly 102 (corresponding to the reference number 1 in FIG. 8 and corresponding to the primary winding 4-6 of the transformer T1 in FIG. 2) The absorption circuit 110 includes a first absorption branch composed of a resistor R11, a resistance R10, a resistance R6, a resistance R8, and a capacitor C3 connected in parallel with each other, and a second absorption branch composed of an inverting diode D4 and an inverting diode D5 connected in parallel with each other. The first absorption branch and the second absorption branch are connected in series. Another end of the first absorption branch is connected to the primary winding 4 of the transformer T1, and another end of the second absorption branch is connected to the primary winding 6 of the transformer T1 and the D pole of the power switch transistor Q1. The absorption circuit 110 absorbs the surge voltage when the control circuit 104 controls the first end of the coupling assembly 102 to transmit electric energy by electromagnetic coupling. It can further be said that the RCD absorption circuit is configured to absorb voltage spikes caused by the leakage inductance of the transformer T1 at the moment that the power switch transistor Q1 is turned off to suppress ringing.

Figure 9:
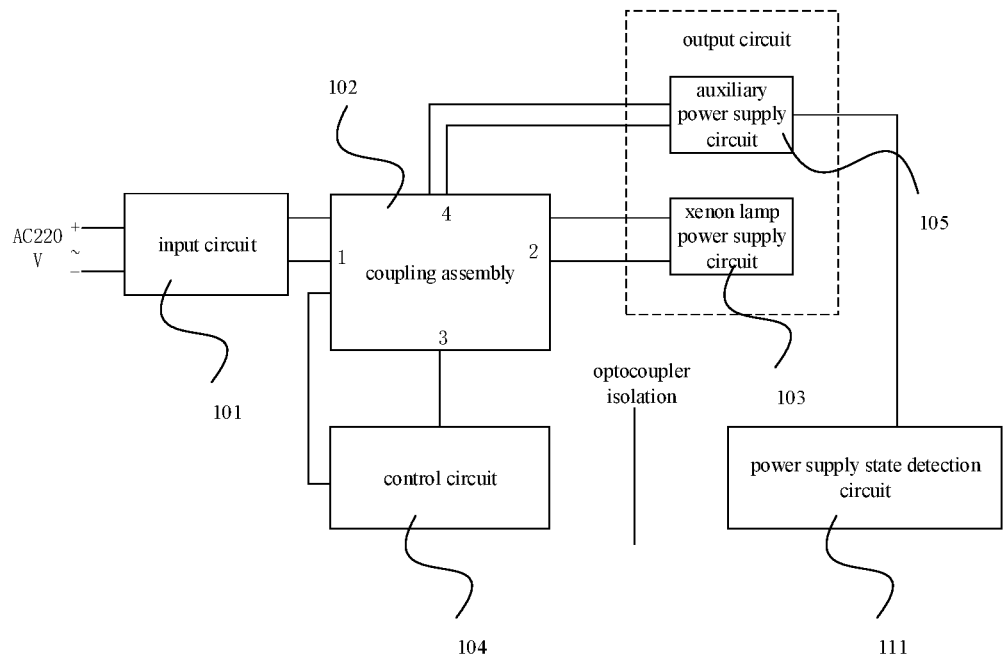
FIG. 9 is an eighth structural schematic diagram of a xenon lamp power supply provided by the application.

FIG. 9 is an eighth structural schematic diagram of a xenon lamp power source provided by the present application. According to a xenon lamp power supply provided by the present application, as shown in FIG. 9, the xenon lamp power supply further includes: a power supply state detection circuit 111 which is connected to the auxiliary power supply circuit 105 to detect whether the output state of the auxiliary power supply circuit 105 is abnormal, and feeds it back to the control circuit 104 when the output state of the auxiliary power supply circuit 105 is abnormal, so that the control circuit 104 can perform abnormal processing.

Referring to FIG. 2 again, the power supply state detection circuit 111 is connected to the auxiliary power supply circuit 105 to receive the weak DC voltage of 12 V output by the auxiliary power supply circuit 105 to detect whether the output state of the auxiliary power supply circuit 105 is abnormal. The power supply state detection circuit 111 adopts an optocoupler detection circuit PH2. A receiving end of the optocoupler detection circuit PH2 (the side of the reference numbers 1-2 of PH2 in FIG. 2) is connected in parallel to a resistor R47 and then is connected in series to a resistor R45, to receive the divided voltage of the weak DC voltage of 12 V output by the auxiliary power supply circuit 105. The divided voltage is coupled to the transmitting end of the optocoupler detection circuit PH2 (the side of the reference numbers 3-4 of PH2 in FIG. 2). The lead wire of the reference number 3 of the transmitting end is connected to the OUTPUT pin of the connector CN4 and the lead wire of the reference number 4 of the transmitting end is connected to the GND pin of the connector CN4 to detect whether the output voltage of the auxiliary power supply circuit 105 is normal. If the voltage output by the auxiliary power supply circuit 105 is normal, the OUTPUT pin of the connector CN4 outputs a low level. If the output of the auxiliary power supply circuit 105 is continuously short-circuited and the output voltage is abnormal, the OUTPUT pin of the connector CN4 outputs a high level. By detecting the output level of the OUTPUT pin of the connector CN4, the working state of the output of the auxiliary power supply circuit 105 can be determined. In addition, when the output state of the auxiliary power supply circuit 105 is abnormal, a feedback can further be provided to the control circuit 104 so that the control circuit 104 can perform abnormal processing.

Figure 10:
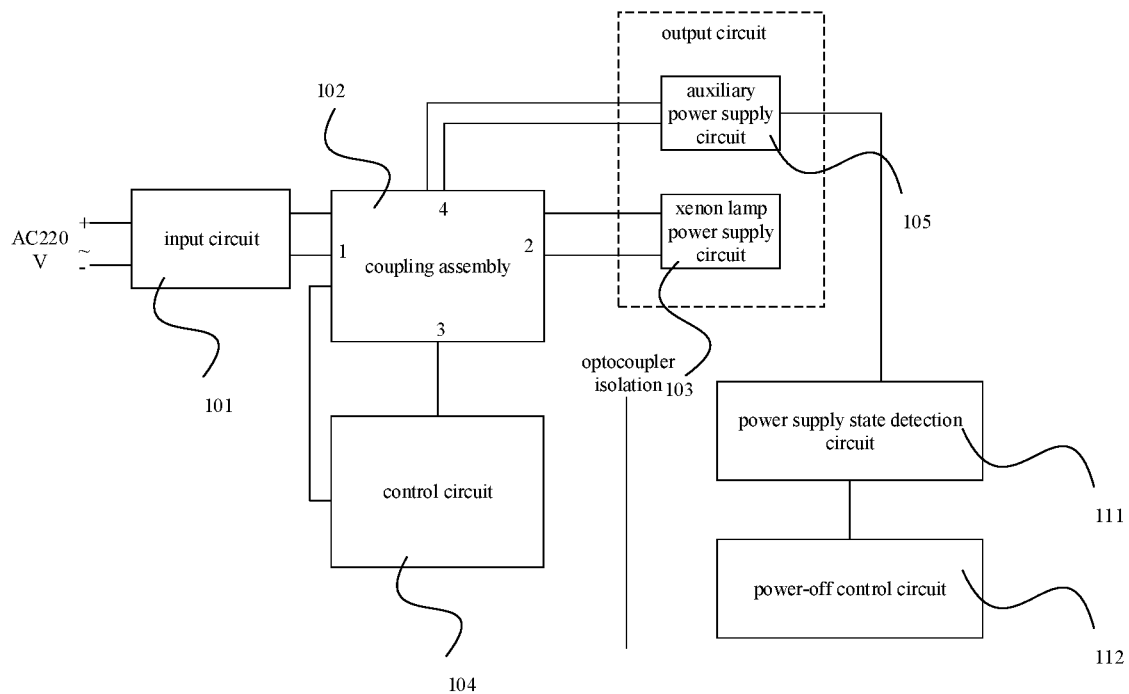
FIG. 10 is a ninth structural schematic diagram of a xenon lamp power supply provided by the application.

FIG. 10 is a ninth structural schematic diagram of a xenon lamp power supply provided by the present application. According to a xenon lamp power supply provided by the present application, as shown in FIG. 10, the xenon lamp power supply further includes: a power-off control circuit 112 which is connected to the power supply state detection circuit 111, to feedback it back to the control circuit 104 when the output state of the auxiliary power supply circuit 105 is abnormal, so that the control circuit 104 can turn off the xenon lamp power supply.

Referring to FIG. 2 again, the power-off control circuit 113 is connected to the power supply state detection circuit 111. The power-off control circuit 113 adopts an optocoupler control circuit PH3, and one end of the lead wire of the reference number 1 of the receiving end (the side of the reference numbers 1-2 of PH3 in FIG. 2) of the optocoupler control circuit PH3 is connected to a resistor R48 and then the INPUT pin of the connector CN4, and one end of the lead wire of the reference number 2 is connected to the GND end of the connector CN4. One end of the lead wire of the reference number 4 of the transmitting end (the side of the reference numbers 3-4 of PH3 in FIG. 2) of the optocoupler control circuit PH3 is grounded, and one end of the lead wire of the reference number 3 is connected in series to a resistor R49 and then is connected to the RT pin of the first power management chip IC1 for feeding back to the control circuit 104 when the output state of the auxiliary power supply circuit 105 is abnormal, so that the control circuit 104 turns off the xenon lamp power supply. Therefore, the xenon lamp power source can be turned on when the xenon lamp is working, and the output of the xenon lamp power source can be turned off when the xenon lamp does not need to work, which facilitates to enlarge the service life of the xenon lamp. And the operation mode of the power off protection of the xenon lamp completely abandons the mechanical protection mode of the relay in traditional technology, with good reliability and long service life. In other words, the xenon lamp power supply provided by this application fully utilizes the protection function and self-recovery function integrated into the power management control, and can use the optocoupler principle to provide the conditions for turning on the protection and canceling the protection of the xenon lamp power supply, to turn on and off the output of the xenon lamp power supply in time, which greatly improves the performance of the xenon lamp power supply.

A purification device for a refrigeration equipment provided in the present application will be described below. The purification device for the refrigeration equipment described below applies the xenon lamp power supply described above, and the specific description can be referred with each other.

Figure 11:
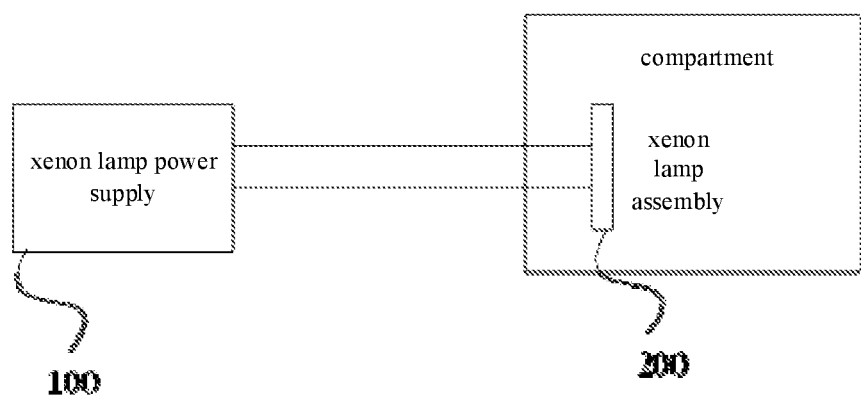
FIG. 11 is a structural schematic diagram of a purification device for a refrigeration equipment provided by the application.

The present application further provides a purification device for a refrigeration equipment, the refrigeration equipment includes a compartment, a refrigeration system for refrigerating the compartment, and a door body for opening and closing the compartment. FIG. 11 is a structural schematic diagram of a purification device for a refrigeration equipment provided by the application, as shown in FIG. 11, the purification device includes:

the above-mentioned xenon lamp power supply 100, configured to supply power to the xenon lamp assembly 200, where the xenon lamp assembly 200 is a xenon lamp provided in the compartment to purify fruits and vegetables stored in the compartment during flashing, to improve food safety.

It should be noted that, in the purification device for the refrigeration equipment provided by the present application, the xenon lamp assembly 200 may be a pulse xenon lamp, or two or more pulse xenon lamps that perform flashing synchronously or alternately. The xenon lamps are all dragged by the xenon lamp power supply 100 described above. The purification function of the purification device includes different purification functions such as sterilization, virus removal, peculiar smell removal, and pesticide residue removal. In an embodiment, the number of pulse xenon lamps in the xenon lamp assembly 200 is adjusted through software control, and the length of the working time of the flashing of each pulse xenon lamp is controlled reasonably. As the purification dose is gradually increased, the purification device can achieve different purification functions of sterilization, virus removal, odor removal, and pesticide residue removal.

Moreover, in addition to the xenon lamp power source and the xenon lamp assembly, the purification device for the refrigeration equipment may include a large-capacity energy-storage capacitor which is connected in parallel to both ends of the xenon lamp power source together with the xenon lamp assembly. The energy-storage capacitor and the xenon lamp assembly together serve as a load element of the xenon lamp power supply circuit (strong DC output circuit) in the xenon lamp power supply, and the energy-storage capacitor stores energy based on the DC voltage of 300 V. After the pulse xenon lamp is triggered and ignited, the energy storage capacitor provides energy for the pulsed xenon lamp for instantaneous consumption when the xenon lamp flashes. After each flashing of the pulse xenon lamp and before the next flashing, the xenon lamp power supply can quickly complete the charging of the energy-storage capacitor, so that the electric energy stored again by the energy-storage capacitor can be used for instantaneous consumption of the next flashing of the pulsed xenon lamp. In addition, the time for the xenon lamp power supply to charge the energy-storage capacitor can be shortened to within 1 s. It is far shorter than the time of at least 10 s usually required to rebuild the voltage of 300 V in the existing power supply technology, and can meet the needs for the pulse xenon lamp to work rapidly and continuously.

The present application further provides a refrigeration equipment, comprising: the purification device according to the above refrigeration equipment.

In an embodiment, the refrigeration equipment may be any common household appliance with a refrigerating function including a purification device, for example, a refrigerator, a freezer, etc., which are installed with the purification device shown in the above embodiment.

According to a refrigeration equipment provided by the present application, the refrigeration equipment is a refrigerator, and the compartment is a refrigerating chamber and/or a temperature variable chamber of the refrigerator.

When the purification device is applied to a refrigerator or freezer, because the storage of fruits, vegetables and other foods usually refers to short-term storage in a refrigerating chamber or a temperature variable chamber with a temperature slightly lower than normal temperature, rather than in a freezing room, the compartment installed with a xenon lamp specifically refers to a refrigerating chamber or a temperature variable chamber of a refrigerator or freezer, which can effectively provide a purified processing space, so that the purification device can purify various foods such as fruits and vegetables stored in the refrigerating chamber or the temperature variable chamber to improve food safety.

The device embodiments described above are only illustrative, where the units described as separate components may or may not be physically separated, and the components shown as units may or may not be physical units, that is, they may be located in one place, or can be distributed over multiple network elements. Some or all of the modules may be selected according to actual needs to achieve the purpose of the solution in this embodiment. Those of ordinary skill in the art can understand and implement it without creative effort.

Finally, it should be noted that the above embodiments are only configured to illustrate the solutions of the present application, but not to limit; although the present application has been described in detail with reference to the foregoing embodiments, those of ordinary skill in the art should understand that: the solutions described in the foregoing embodiments still can be modified, or some features thereof can be equivalently replaced; and these modifications or replacements do not make the essence of the corresponding solutions deviate from the spirit and scope of the solutions in the embodiments of the present application.

What is claimed is:

1. A xenon lamp power supply, comprising:
an input circuit, including an AC input end and a DC output end and being configured to convert an AC input from the AC input end to a DC output from the DC output end;
a coupling assembly, wherein a first end of the coupling assembly is connected to the DC output end;
an output circuit, including a xenon lamp power supply circuit which is connected to a second end of the coupling assembly, to convert an electric energy from the second end to a strong DC for powering a xenon lamp; and
a control circuit, connected to the first end and a third end of the coupling assembly respectively and configured to control an electric energy of the first end of the coupling assembly to transmit the electric energy to the second end and the third end of the coupling assembly by electromagnetic coupling, wherein the third end of the coupling assembly supplies power to the control circuit;
wherein the output circuit further comprises an auxiliary power supply circuit, wherein the auxiliary power supply circuit is connected to a fourth end of the coupling assembly and is configured to convert an electric energy from the fourth end to a weak DC and output the weak DC.

2. The xenon lamp power supply according to claim 1, further comprises: a feedback circuit, wherein the feedback circuit is connected to the xenon lamp power supply circuit and the auxiliary power supply circuit respectively to detect a voltage of the strong DC output by the xenon lamp power supply circuit, and cooperates with the weak DC provided by the auxiliary power supply circuit to generate a detection signal of the voltage of the strong DC output by the xenon lamp power supply circuit, and feeds back the detection signal to the control circuit.

3. The xenon lamp power supply according to claim 2, wherein the control circuit is configured to adjust an on-off duty cycle of the first end of the coupling assembly according to the detection signal, to change the voltage of the strong DC output by the xenon lamp power supply circuit.

4. The xenon lamp power supply according to claim 2, further comprises: a shielding circuit, wherein one end of the shielding circuit is connected to the control circuit and another end of the shielding circuit is grounded, and the shielding circuit is configured to shield an open-circuit state of the feedback circuit.

5. The xenon lamp power supply according to claim 1, further comprises an overvoltage protection circuit, wherein the overvoltage protection circuit is connected to the control circuit and a fifth end of the coupling assembly respectively, and is configured to perform overvoltage protection on the control circuit when the strong DC output by the xenon lamp power supply circuit is greater than a preset value, wherein the fifth end of the coupling assembly is in the same phase as the first end of the coupling assembly.

6. The xenon lamp power supply according to claim 1, further comprises: a startup circuit, wherein the startup circuit is connected to the control circuit and the input circuit respectively, to start the control circuit through the electric energy provided by the input circuit.

7. The xenon lamp power supply according to claim 1, further comprises: an absorption circuit, wherein the absorption circuit is provided between the control circuit and the first end of the coupling assembly, to absorb a surge voltage when the control circuit controls the first end of the coupling assembly to transmit an electric energy by electromagnetic coupling.

8. The xenon lamp power supply according to claim 1, further comprises: a power supply state detection circuit, wherein the power supply state detection circuit is connected to the auxiliary power supply circuit to detect whether an output state of the auxiliary power supply circuit is abnormal, and feeds it back to the control circuit when the output state of the auxiliary power supply circuit is abnormal, and the control circuit performs abnormal processing.

9. The xenon lamp power supply according to claim 8, further comprises:
a power-off control circuit, wherein the power-off control circuit is connected to the power supply state detection circuit, to perform feedback to the control circuit when the output state of the auxiliary power supply circuit is abnormal, and the control circuit turns off the xenon lamp power supply.

10. A purification device for a refrigeration equipment, wherein the refrigeration equipment comprises a compartment, a refrigeration system for refrigerating the compartment, and a door body for opening and closing the compartment, wherein the purification device comprises:
the xenon lamp power supply according to claim 1, to supply power to the xenon lamp assembly, wherein the xenon lamp assembly is a xenon lamp provided in the compartment to purify food stored in the compartment during flashing.

11. A refrigeration equipment, comprising: a purifying device for a refrigeration equipment according to claim 10.

12. The refrigeration equipment according to claim 11, wherein the refrigeration equipment is a refrigerator, and the compartment is a refrigerating chamber and/or a temperature variable chamber of the refrigerator.

* * * * *